(12) United States Patent
Lee

(10) Patent No.: US 8,414,538 B2
(45) Date of Patent: Apr. 9, 2013

(54) SINGLE-HANDED SYRINGE

(76) Inventor: Paul J. Lee, Clarence, NY (US)

( * ) Notice: Subject to any disclaimer, the term of this patent is extended or adjusted under 35 U.S.C. 154(b) by 703 days.

(21) Appl. No.: 12/129,950

(22) Filed: May 30, 2008

(65) Prior Publication Data

US 2008/0306448 A1 Dec. 11, 2008

Related U.S. Application Data

(60) Provisional application No. 60/940,764, filed on May 30, 2007.

(51) Int. Cl.
*A61M 5/00* (2006.01)
*A61M 5/315* (2006.01)

(52) U.S. Cl. .......... 604/191; 604/218; 604/232

(58) Field of Classification Search .......... 604/218–231, 604/190, 82–84, 191
See application file for complete search history.

(56) References Cited

U.S. PATENT DOCUMENTS

| | | | |
|---|---|---|---|
| 3,990,446 A | 11/1976 | Taylor | |
| 4,248,228 A | 2/1981 | Silver | |
| 4,469,482 A | 9/1984 | Lissenburg et al. | |
| 4,484,915 A | 11/1984 | Tartaglia | |
| D279,407 S | 6/1985 | Hubbard | |
| 4,534,542 A | 8/1985 | Russo | |
| 4,711,250 A | 12/1987 | Gilbaugh, Jr. et al. | |
| 4,766,908 A | 8/1988 | Clement | |
| 4,813,433 A | 3/1989 | Downey | |
| 4,973,316 A | 11/1990 | Dysarz | |
| 5,135,511 A | 8/1992 | Houghton et al. | |
| 5,332,094 A | 7/1994 | Cilia et al. | |
| 5,498,246 A | 3/1996 | Deutchman et al. | |
| 5,582,595 A | 12/1996 | Haber et al. | |
| 5,830,152 A | 11/1998 | Tao | |
| 5,833,668 A | 11/1998 | Aguilar | |
| 5,860,949 A | 1/1999 | Chen | |
| 6,231,550 B1 | 5/2001 | Laughlin | |
| 6,638,258 B2 * | 10/2003 | Schwartz et al. | 604/247 |
| 6,641,555 B1 | 11/2003 | Botich et al. | |
| 6,669,672 B2 | 12/2003 | Wu | |
| 6,719,735 B1 | 4/2004 | Gammon | |
| 6,929,620 B2 * | 8/2005 | Hasegawa | 604/82 |
| 7,118,554 B2 | 10/2006 | Sibbitt | |
| 7,118,556 B2 | 10/2006 | Nerney | |
| 2003/0069543 A1 * | 4/2003 | Carpenter et al. | 604/190 |
| 2003/0187406 A1 | 10/2003 | Spofforth | |
| 2005/0215958 A1 | 9/2005 | Hawthorne | |

FOREIGN PATENT DOCUMENTS

| | | |
|---|---|---|
| EP | 0080793 | 6/1983 |
| EP | 0254765 | 2/1988 |
| EP | 0279956 | 8/1988 |
| EP | 0472023 | 2/1992 |
| JP | 2006043354 | 9/2007 |

\* cited by examiner

*Primary Examiner* — Kevin C Sirmons
*Assistant Examiner* — Imani Hayman
(74) *Attorney, Agent, or Firm* — Jaeckle Fleischmann & Mugel, LLP

(57) ABSTRACT

The present invention provides a syringe device including a needle, a syringe body, and a syringe adaptor between the needle and the syringe body. This syringe adaptor includes a reservoir and a plunger configured to move into and out of the reservoir in a direction perpendicular to the longitudinal direction of the needle. The position and direction of travel of the plunger in the syringe adaptor allows a user of the syringe of the present invention to safely and accurately operate the syringe with one hand.

15 Claims, 5 Drawing Sheets

SINGLE-HANDED SYRINGE

CROSS-REFERENCE TO RELATED APPLICATIONS

This application is based on, and claims priority to, U.S. Provisional Application No. 60/940,764, filed May 30, 2007, the entire contents of which are fully incorporated herein by reference.

FIELD OF THE INVENTION

The invention relates to devices for aspirating and injecting fluids, and particularly syringes for aspirating/injecting fluids.

BACKGROUND OF THE INVENTION

In the medical field, syringes are used for a variety of functions. However, syringes generally operate in one of two manners: (1) aspirating, or extracting a fluid from a subject; and (2) injecting a fluid into a subject. Conventional syringes require two separate components for aspirating or injecting a fluid, specifically a syringe body and a plunger. The syringe body includes an attached needle on one end and a reservoir on the other. The reservoir is used to hold either a fluid to be injected or a fluid that has been aspirated. The plunger fits into the reservoir end forming an airtight seal and thus creating a vacuum in the reservoir. By moving the plunger, a person operating the syringe can either inject a fluid by moving the plunger further into the reservoir, or aspirate a fluid by moving the plunger further out of the reservoir.

A conventional syringe has inherent drawbacks. Some applications of a syringe require steady application of pressure both at the needle end and at the plunger. Injecting a fluid directly into a blood vessel, for example, requires steadiness at the needle. By applying pressure to the end of the plunger, any small lateral movements of the plunger results in an exaggerated movement at the needle tip. This exaggerated movement can damage or destroy a blood vessel. Another situation involves injection or aspiration from a small organ such as the eye. Any movement may induce unwanted side effects.

Another drawback of conventional syringes is that some applications require the use of two hands. If a patient is moving uncontrollably (e.g., due to extensive trauma or shock), a person operating the syringe may need to use one hand to steady the needle tip and ensure the needle remains inserted into the subject being injected, while the operator's second hand is used to operate the plunger end. Situations like this typically require an assistant to stabilize the subject being injected while the operator controls the syringe.

Aspirating with a conventional syringe nearly always requires the use of two hands, unless the syringe has been previously modified. One hand holds the syringe body steady while the second hand extracts the plunger from the reservoir end of the syringe body. The movements required to aspirate with a typical syringe dictate that two hands be used to perform the aspirating safely.

In the above discussion, the common fundamental problem with traditional syringes is the inability to safely operate the syringe with one hand during specific applications such as injecting a moving subject or aspirating fluid from a subject. Another fundamental problem is the inability of the traditional design to address injection/aspiration into a small delicate organ such as the eye with one hand while maintaining stability of the eye/head.

SUMMARY OF THE INVENTION

In accordance with a first aspect of the invention a syringe device is provided comprising a needle having a longitudinal passageway throughout, a syringe body, and a syringe adaptor between the needle and the syringe body. This syringe adaptor includes a reservoir and a plunger configured to move into and out of the reservoir in a direction perpendicular to the longitudinal passageway throughout the needle.

In accordance with a second aspect of the invention a syringe device is provided comprising a needle having a longitudinal passageway throughout, a syringe body, and a syringe adaptor between said needle and said syringe body. The syringe adaptor includes a plurality of adaptor bodies, each adapter body including a reservoir and a plunger configured to move into and out of the reservoir in a direction perpendicular to the longitudinal passageway throughout the needle.

DETAILED DESCRIPTION OF THE INVENTION

Figure 1A:
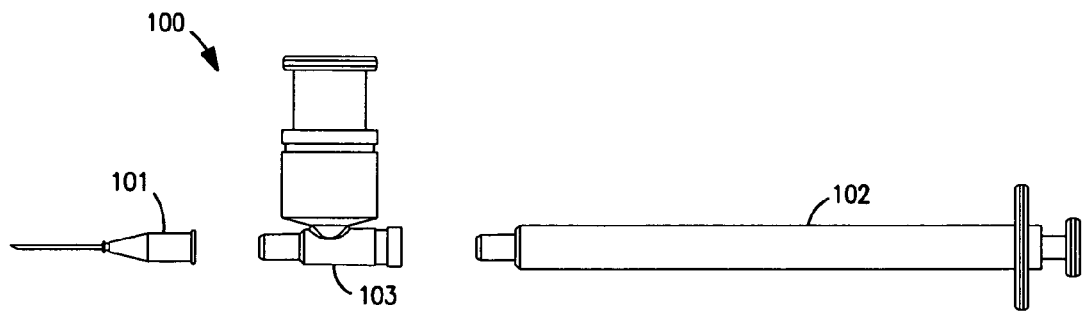
FIG. 1A illustrates a typical syringe with an adaptor for one-handed syringe use according to the principles of the present invention.

The present invention provides a syringe device with an adaptor that modifies a typical syringe to change the overall structure of the syringe to one better suited to safe one-handed operation. FIG. 1A is a view of the three main components of syringe 100. A conventional syringe such as those described in the background includes needle 101 and syringe body 102. Needle 101 includes a longitudinal passageway through which a fluid is either injected into or aspirated from a subject. The present invention places an adaptor 103 between needle 101 and body 102 to facilitate one-handed operation of syringe 100 such that the plunger of the syringe causing the injection or aspiration moves in a direction perpendicular to the passageway through the needle. This design permits a user to grip the syringe similarly to that of holding a pen, which is more natural and ergonomic. Lateral movement is minimized because the perpendicular force generated by pushing in on the plunger is counterbalanced by an equal and opposite force provided by the thumb or ball of the user's hand that is positioned opposite the plunger.

Figure 2:
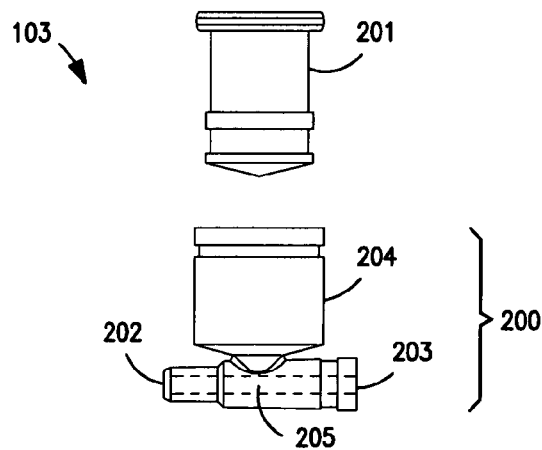
FIG. 2 is an exploded view of the adaptor for one-handed syringe use of FIG. 1A according to the principles of the present invention.

FIG. 2 is an exploded view of adaptor 103 of FIG. 1A. The adaptor 103 comprises two main pieces, adaptor body 200 and plunger 201. Adaptor body 200 comprises four components, namely, male luer connector 202, female luer connector 203, a channel 205 therebetween, and adapter barrel 204. Male luer connector 202 provides a connection point for attaching a needle to adaptor 103, such as needle 101 from FIG. 1A. Similarly, female luer connector 203 provides a connection point for attaching a syringe body to adaptor 103, such as syringe body 102. Luer connectors are merely exemplary and any reasonable connector type of connectors can be used, such as a screw connector.

The male luer and the female luer collectively define the passageway 205 therebetween parallel to the passageway through the needle. It should be noted that syringe body 102 is shown by way of example. Other components could be attached to female luer 203 such that the direction of fluid is directed into or out of male luer 202, and subsequently, the passageway through the needle.

The third component of adaptor body 200 is adaptor barrel 204 in fluid communication with this passageway. Adapter barrel 204 contains a reservoir for holding the fluid to be injected with the syringe or the fluid that has been aspirated into the syringe. For added convenience, adaptor barrel 204 can be transparent with one or more volume indicators, e.g., 1 cubic centimeter (cc), imprinted on the side. Other design choices for adaptor barrel 204 should be obvious to one of ordinary skill in the art and will not be further discussed herein.

Adaptor 103 further includes a plunger 201. Plunger 201 is shaped such that, upon insertion into adaptor barrel 204, an air tight seal is created between the wall of the reservoir of adaptor barrel 204 and plunger 201 allowing for injection or aspiration of a fluid.

Referring back to FIG. 1A, adaptor 103 enables a person to safely use syringe 100 with one-hand. Particularly, the design of adaptor 103 and its positioning relative to the needle 101 and syringe body 102 permits the user to hold the syringe 100 close to the needle with his or her hand on the plunger. Thus, the person using the syringe has greater control over the needle when inserting the needle into a subject, and also has greater control over the syringe once the needle is in the subject because the user grasps the syringe at or close to the geometric center of the syringe. Additionally, by orienting the direction of movement of the adaptor plunger 201 to a direction perpendicular to that of the direction of the passageway through the needle, the person using the syringe can hold the syringe body between the thumb and middle finger like a pen, as shown in FIG. 1B, and easily depress the plunger with his or her index finger to inject a fluid into a subject.

Figure 1B:
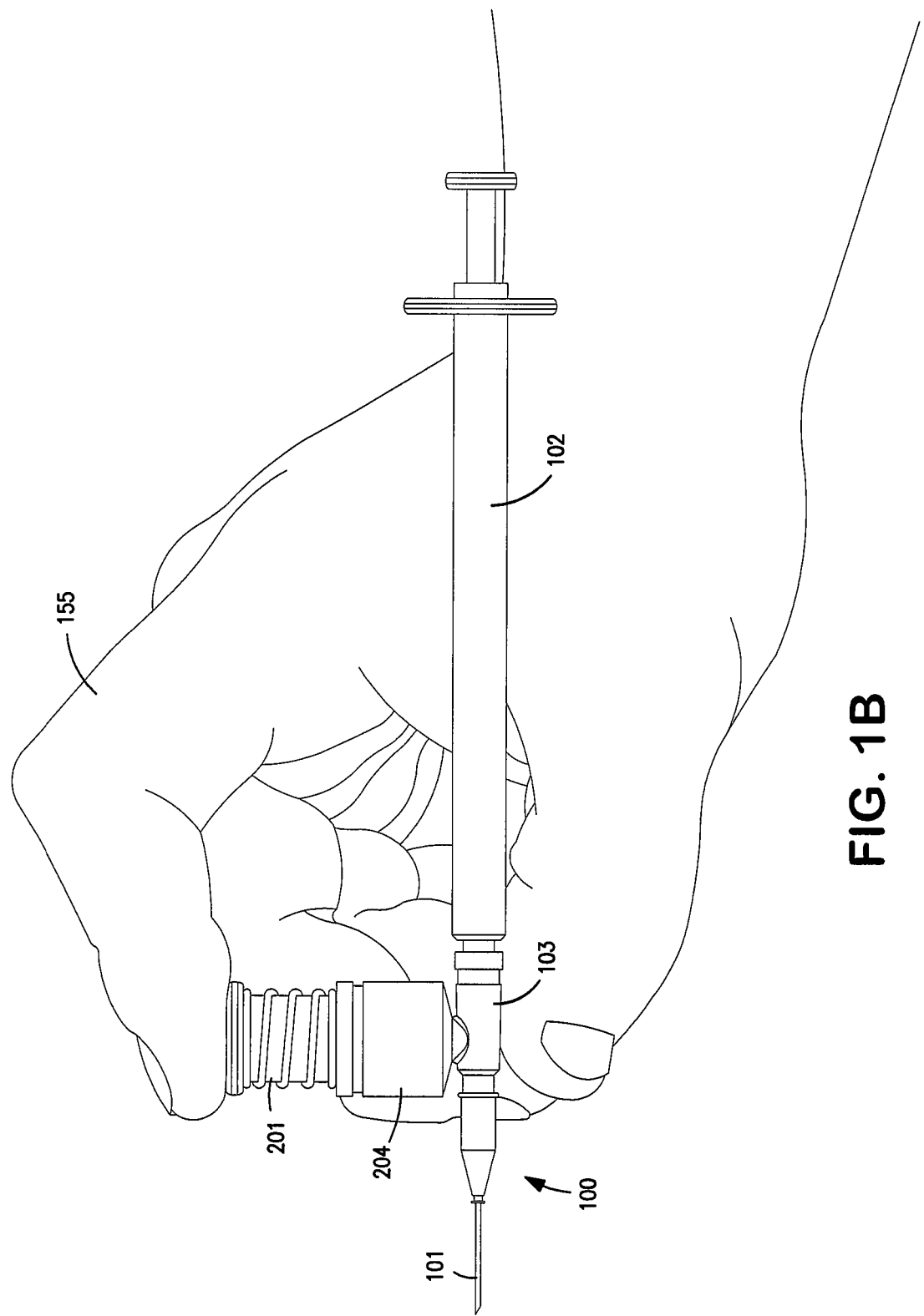
FIG. 1B is a view of a hand holding the syringe of FIG. 1A being held in a hand in accordance with one embodiment of the invention.

FIG. 1B illustrates a hand 155 holding syringe 100. The person holding syringe 100 rests his or her index finger on plunger 201 so as to be able to apply pressure to plunger 201, when desired. The plunger will travel in a direction perpendicular to the needle 101. As discussed above, by moving the placement of the operator's hand closer to the needle, better control of the syringe is possible in one-handed operation.

Figure 3:
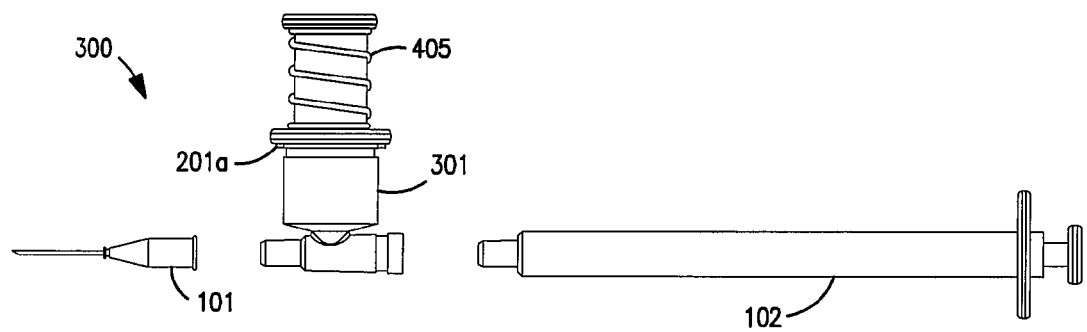
FIG. 3 illustrates a syringe with an adaptor having an integrated spring for one-handed syringe use according to the principles of the present invention.
Figure 4:
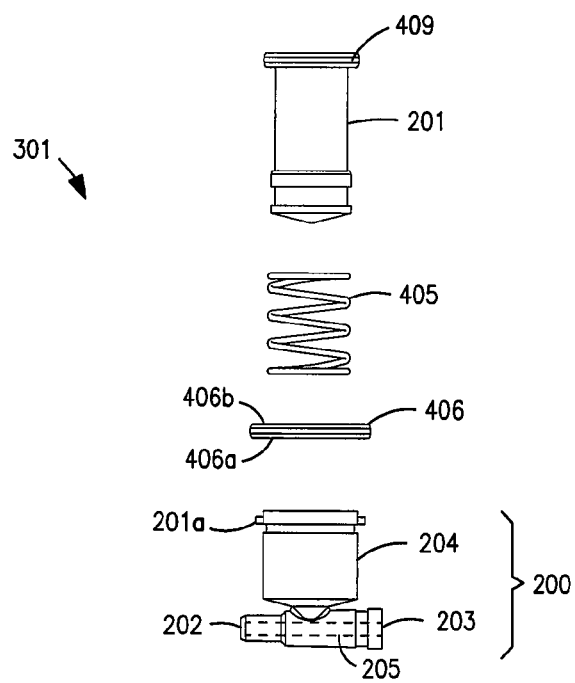
FIG. 4 is an exploded view of the adaptor having an integrated spring for one-handed syringe use according to the principles of the present invention.

FIG. 3 illustrates another embodiment of a syringe in accordance with the principles of the present invention more particularly adapted to facilitate aspiration although also useful for injection. FIG. 4 shows an exploded view of aspirating syringe adaptor 301 of FIG. 3. Syringe 300 is similar in structure to syringe 100 of FIG. 1A in that it has three main components: needle 101; syringe barrel 102 and aspirating syringe adapter 301. Aspirating syringe adaptor 301 further includes a spring 405 to assist in one-handed aspirating of fluids.

Similar to syringe adaptor 103 illustrated in FIG. 2, aspirating syringe adapter 301 comprises an adaptor body 200, a plunger 201, a male luer connector 202, female luer connector 203, passageway 205, and adaptor barrel 204. Syringe adaptor 301 further comprises spring 405 and adaptor cap 406. Spring 405 may be a coil spring loosely coiled around plunger 201. Adaptor cap 406 is slipped over plunger 201 and positioned so that the bottom surface 406a of adaptor cap 406 rests on flange 201a of plunger 201. The bottom of the spring 405 rests against the upper surface 406a of adaptor cap 406. When the syringe adaptor 301 is assembled, the adaptor cap 406 is welded, bonded, or otherwise attached to the adaptor barrel 204 as shown in FIG. 3. Thus, spring 405 is held to the syringe adaptor 301 by virtue of being trapped between top flange 409 of plunger 201 and adaptor cap 406. The spring 405 is slightly compressed when the plunger 201 is fully extended from the adaptor barrel 204. Once fitted around plunger 201 and attached to adaptor barrel 204, spring 405 functions to provide resistance against plunger 201 when being depressed, which may help moderate the pressure the user must apply to inject or aspirate a fluid as well as to extract plunger 201 from adaptor barrel 204 when plunger 201 has been depressed, which may help moderate the pressure the user must apply to inject a fluid and pressure has been released. Flange 201a in conjunction with adaptor cap 406 being attached to the adaptor barrel 204 also prevents the plunger from being ejected from the adaptor barrel by the force of the spring. This design provides for a syringe capable of safe and convenient one handed aspiration of a fluid from a subject.

Referring back to FIG. 3, a person using syringe 300 to aspirate a fluid from a subject would follow a procedure similar to that followed for using syringe 100 of FIG. 1A. To aspirate, however, prior to inserting the needle into the subject, the person using the syringe first depresses the plunger against the outwardly biasing force of the spring 405, such that a large portion of the air in the adaptor barrel is expelled. Still depressing the plunger, the person using syringe 300 then sticks the needle into the subject. Similar to the discussion of syringe 100 in FIG. 1A, by virtue of holding syringe 300 at a location close to the tip of the needle yet still close to the geometric center of the syringe, the person using the syringe has greater control over the needle resulting in a more accurate needle location. During a typical aspirating procedure, such as collecting a blood sample, it is important that the needle accurately penetrates a blood vessel. By providing additional control, the present invention provides this needed accuracy. Once the needle is stuck in the subject, the person using the syringe simply releases the finger pressure from the plunger so that the spring biases the plunger 201 away from the adaptor barrel 204. As a result of the vacuum created by the seal between the plunger and the adaptor barrel and the movement of the plunger out of the internal volume of the adaptor barrel 204, fluid is aspirated from the subject through the needle into the adaptor barrel.

Both FIGS. 2 and 4 show an adaptor barrel with a 1 cc. capacity. This volume is merely shown by way of example and is not meant to limit the invention. Other sizes of adaptor barrels and plungers can be used depending on the volume of fluid to be injected or aspirated.

Figure 5A:
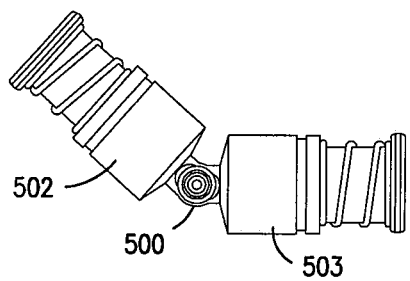
FIG. 5A is a first view of an adaptor having multiple reservoirs and plungers for one-handed syringe use of FIG. 3 according to the principles of the present invention.
Figure 5B:
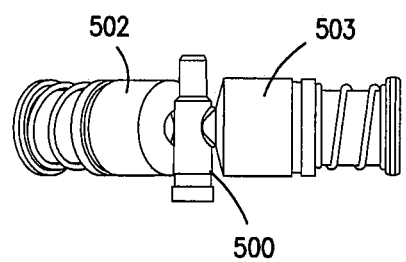
FIG. 5B is a second view of the adaptor having multiple reservoirs and plungers for one-handed syringe use of FIG. 5A according to principles of the present invention.
Figure 5C:
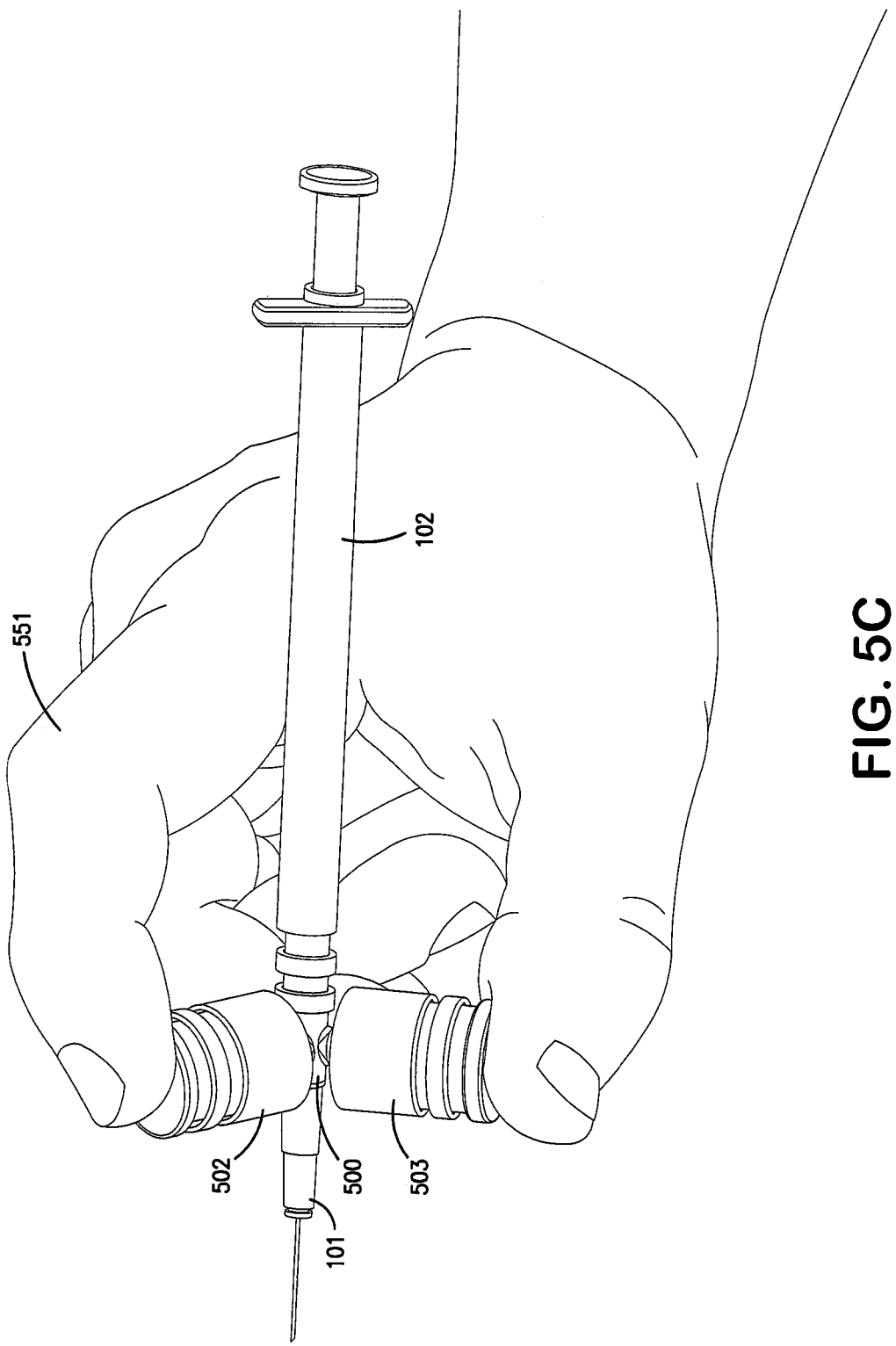
FIG. 5C is a view of the syringe of FIG. 5A being held in a hand in accordance with one embodiment of the invention.

In other embodiments, multiple barrels can be fitted onto a syringe adaptor. FIGS. 5A, 5B, and 5C illustrate several views of an alternate syringe adaptor 500 that can be mounted between a needle 101 and syringe body 102 having two adaptor barrels 502 and 503 arranged in a V formation. By providing multiple adaptor barrels, multiple medications can be given in a single injection or a larger amount of fluid can be aspirated at one time. With reference to FIG. 5C in particular, the person using a syringe with syringe adaptor 500 can hold the syringe in his or her hand 551 like a pen and depress the plunger with his or her thumb and index finger, as shown in FIG. 5C. However, any combination of fingers allowing the user the maximum control may be used.

Another possible modification would be to replace the adaptor plungers with a single, flexible membrane fitted over the top of the adaptor barrels for creating a vacuum inside the adaptor barrels similar to the one created by the plungers. By filling the barrel first with a fluid and sticking the needle into a subject, depressing the membrane would inject the fluid into the subject. Conversely, to aspirate a fluid from a subject, the membrane would first be depressed, then the needle would be inserted into the subject and the pressure removed from the membrane. The resulting pull from the membrane returning to its normal position would result in fluid being aspirated from the subject into the adaptor barrel.

The new design allows a finer and more ergonomic control over injection and aspiration from a delicate organ such as the eye where any small movement is magnified and finer control is essential. The new design allows one hand to be freed to stabilize the patient or organ as necessary.

Having thus described several particular embodiments of the invention, various alterations, modifications, and improvements will readily occur to those skilled in the art. Such alterations, modifications, and improvements as are made obvious by this disclosure are intended to be part of this description though not expressly stated herein, and are intended to be within the spirit and scope of the invention. Accordingly, the foregoing description is by way of example only, and not limiting. The invention is limited only as defined in the following claims and equivalents thereto.

The invention claimed is:

1. A syringe device comprising:
   a needle having a first longitudinal passageway throughout;
   a syringe body; and
   a syringe adaptor connected between said needle and said syringe body, said syringe adaptor comprising:
      an adaptor body including a reservoir;
      a manually operable plunger oriented to move into and out of said reservoir in a direction perpendicular to the longitudinal passageway throughout said needle; and
      a second passageway providing fluid communication between said first longitudinal passageway in said needle and said reservoir so as to permit expression of fluid in said reservoir from said needle through said first passageway and aspiration of fluid into said reservoir from said needle through said first passageway by operation of said plunger.

2. The syringe device of claim 1 wherein said plunger includes a spring to assist in extracting said plunger from said reservoir.

3. The syringe device of claim 2 wherein said adaptor body, said plunger and said reservoir are separable from each other.

4. The syringe device of claim 3 wherein said syringe adaptor includes a male luer connector and a female luer connector.

5. The syringe device of claim 4 wherein said male luer connector is adapted to attach said needle to said adaptor.

6. The syringe device of claim 4, wherein said female luer connector is adapted to attach said syringe body to said syringe adaptor.

7. The syringe device of claim 1 wherein the adapter comprises a plurality of reservoirs, each reservoir having a plunger configured to move into and out of said reservoir in a direction perpendicular to the longitudinal passageway throughout said needle.

8. A syringe adaptor device comprising:
   a reservoir;
   a plunger;
   an adaptor body including a first passageway in fluid communication with said reservoir, a connector for connecting said adaptor to a needle having a second, longitudinal passageway with said second, longitudinal passageway longitudinally oriented in a first direction relative to said adaptor body, said second, longitudinal passageway for injecting or aspirating fluid through said needle, said first passageway providing fluid communication between said connector and said reservoir so as to permit expression of fluid in said reservoir from said connector and aspiration of fluid into said reservoir from said connector by operation of said plunger; and
   the plunger oriented to move into and out of said reservoir in a direction perpendicular to said first direction.

9. The syringe adaptor device of claim 8 wherein said plunger includes a spring to assist in extracting said plunger from said reservoir.

10. The syringe adaptor device of claim 8 wherein said syringe adaptor device further comprises a second connector in fluid communication with said first passageway, said second connector adapted to attach a syringe body to said syringe adaptor device.

11. The syringe adaptor device of claim 8 wherein said adaptor body, said reservoir and said plunger are separable from each other.

12. A syringe device comprising:
   a needle having a first longitudinal passageway throughout;
   a syringe adaptor comprising:
      an adaptor body including a reservoir;
      a manually operable plunger oriented to move into and out of said reservoir in a direction perpendicular to the longitudinal passageway throughout said needle; and
      a second passageway providing fluid communication between said first longitudinal passageway in said needle and said reservoir so as to permit expression of fluid in said reservoir from said needle through said first passageway and aspiration of fluid into said reservoir from said needle through said first passageway by operation of said plunger.

13. The syringe device of claim 12 wherein said plunger includes a spring to assist in extracting said plunger from said reservoir.

14. The syringe device of claim 13 wherein said adaptor body, said plunger and said reservoir are separable from each other.

15. The syringe device of claim 12 wherein the adapter comprises a plurality of reservoirs, each reservoir having a plunger configured to move into and out of said reservoir in a direction perpendicular to the longitudinal passageway throughout said needle.

* * * * *